(12) United States Patent
Ide et al.

(10) Patent No.: US 6,514,212 B1
(45) Date of Patent: Feb. 4, 2003

(54) HEMADYNAMOMETER (75) Inventors: Kazuhiro Ide, Kadoma (JP); Daisuke Morikawa, Kadoma (JP); Fumio Kitagawa, Kadoma (JP); Satoshi Nakayama, Kadoma (JP); Takahiro Kurihara, Kadoma (JP); Manabu Hamamoto, Kadoma (JP); Shinichi Fumuro, Kadoma (JP); Kouichi Okada, Kadoma (JP); Tomohiro Kami, Kadoma (JP)

(73) Assignee: Matsushita Electric Works, Ltd., Osaka (JP)

( * ) Notice: Subject to any disclaimer, the term of this patent is extended or adjusted under 35 U.S.C. 154(b) by 15 days.

(21) Appl. No.: 09/589,019

(22) Filed: Jun. 7, 2000

(30) Foreign Application Priority Data

Jun. 11, 1999 (JP) .......................................... 11-166023

(51) Int. Cl.⁷ ................................................ A61B 5/00
(52) U.S. Cl. ...................... 600/490; 600/500; 600/485; 600/499
(58) Field of Search ................................ 600/485, 490, 600/492, 499–500, 503

(56) References Cited

U.S. PATENT DOCUMENTS

| | | | | |
|---|---|---|---|---|
| 4,605,010 A | * | 8/1986 | McEwen | 600/499 |
| 4,860,761 A | * | 8/1989 | Yamasawa et al. | 600/499 |
| 6,231,517 B1 | * | 5/2001 | Forstner | 600/485 |

FOREIGN PATENT DOCUMENTS

JP          61-11019          6/1984

* cited by examiner

*Primary Examiner*—Robert L. Nasser
(74) *Attorney, Agent, or Firm*—Lynn & Lynn (57) ABSTRACT

A hemadynamometer has an air bag designed for attaining oppression or ischemia of radial artery only without oppressing ulnar artery, with a length of the bag made, when the bag is wound on a user's wrist on its radial side starting from such hard organization area as tendons on palm side of the wrist through the radial artery, to reach at least styloid process of radius but not to reach the ulnar artery, and with a width set for locally oppressing the radial artery at least substantially right above the styloid process of radius in longitudinal direction of the wrist.

3 Claims, 10 Drawing Sheets

HEMADYNAMOMETER

BACKGROUND OF THE INVENTION

This invention relates to a hemadynamometer suitable for measuring at the user's wrist such living body information as blood pressure; pulse and so on and, more particularly, to a hemadynamometer having an air bag featured in its structure for oppressing the wrist.

DESCRIPTION OF RELATED ART

Generally, the hemadynamometer employing an oppression method by means of the air bag is so constituted that the air bag is pressurized to be inflated until the artery is completely closed, thereafter the pressure in the bag is gradually deflated to catch pulsating signals of the artery superposed on oppressing force of the air bag, and the highest, lowest and average blood pressures are discriminated as based on amplitude variation in the signals. There has been known an electronic hemadynamometer for automatically measuring the blood pressure at such body portion for oppression as an arm and a wrist. Generally, in the wrist, there are extending a radius, an ulna, tendons, muscle and two thick arteries called radial artery and ulnar artery which are branched from an upper arm artery. With the wrist-type hemadynamometer employing the oppression by means of the air bag, these two arteries are simultaneously subjected to an ischemia with the air bag inflated, and the blood pressure is discriminated from the pulse signal caught by deflating the air bag.

Since in this case a large oppression force of the air bag is required for the simultaneous ischemia of the two arteries, the user is forced to have a large oppressive sensation. Further, as the ulnar artery is generally present at a deeper position than the radial artery from the surface of the wrist and the pulse signal of the ulnar artery appears earlier than that of the radial artery, and an error is apt to occur in the blood pressure discrimination. It has been attempted, therefore, to attain the ischemia only of either the radial or ulnar artery for the blood pressure discrimination. In Japanese Patent Laid-Open Publication No. 61-11019, for example, a hemadynamometer having an air bag which oppresses only the radial artery has been disclosed, in which the air bag of a shape elongated in the lengthwise direction of the wrist along the radial artery is made not to contact the tendon nor the radius, with a length in the peripheral direction of the wrist made larger than a diameter of the radial artery but smaller than a distance between the tendon and the radius on the palm side of the wrist. Here, as the radial artery extends between the tendon on the palm side of the wrist and the styloid process of radius to be the closest to the surface of the living body at a position adjacent to the styloid process of radius, it becomes possible to have the radial artery subjected to the ischemia under the minimum pressure, by oppressing over a length smaller than the distance between the tendon and the radius and a portion adjacent to the styloid process of radius.

However, the position of the radial artery involves the individual difference, such that the radial artery is not present between the tendon and the styloid process of radius but is running over and outside the styloid process of radius, upon which the radial artery cannot be subjected to the ischemia with the air bag of the type disclosed in the JP Laid-Open Pub. 61-11019. Further, the ulnar artery also runs in general between the tendon on the palm side of the wrist and the styloid process of ulna, but the individual difference shows that there is an event where the radial artery is running outside the styloid process of ulna. Further, since the conventional air bags are kept not to contact the tendon and radius, there have been problems that positional deviation of the air bag is apt to occur as the inflation advances, the artery of which the ischemia is expected is apt to escape within the wrist, and the degree of ischemia is deteriorated.

SUMMARY OF THE INVENTION

An object of the present invention is to provide a hemadynamometer which has overcome the forgoing problems of the known devices and is capable of discriminating an accurate blood pressure with a high precision of discrimination, sufficiently in response to the individual difference in the position of the arteries in the wrist, eliminating any positional deviation of the air bag or escaping of the arteries during the pressurizing, reducing any oppressive sensation to the user and thus any burden to the user, and executing the ischemia with such ideal air bag.

According to the present invention, the above object is achieved by providing a hemadynamometer attaining arterial oppression for ischemia with air bag wound on a wrist in its circumferential direction, wherein the air bag is adapted for not oppression of one of two arteries in a wrist of the user which are possibly subject to ischemia but for at least one of oppression and ischemia of only the other artery, with a length of the air bag enough, when the air bag is wound on the wrist from such hard organization area as tendons on palm side as a start point towards the other artery subject to ischemia, for passing over the other artery and reaching at least styloid process of one of two bones at the wrist but not reaching said one of the arteries, and a width enough for locally oppressing the other artery subject to ischemia at a portion substantially right above the styloid process of the bone on the other artery side with respect to lengthwise direction of the wrist.

Other object and advantage of the present invention shall be made clear as the description advances with reference to certain embodiments shown in accompanying drawings.

While the present invention shall now be described with reference to the respective embodiments shown in the drawings, it should be appreciated that the intention is not to limit the invention only to these embodiments shown but rather to include all alterations, modifications and equivalent arrangements possible within the scope of appended claims.

DETAILED DESCRIPTION OF THE PREFERRED EMBODIMENTS

Figure 1:
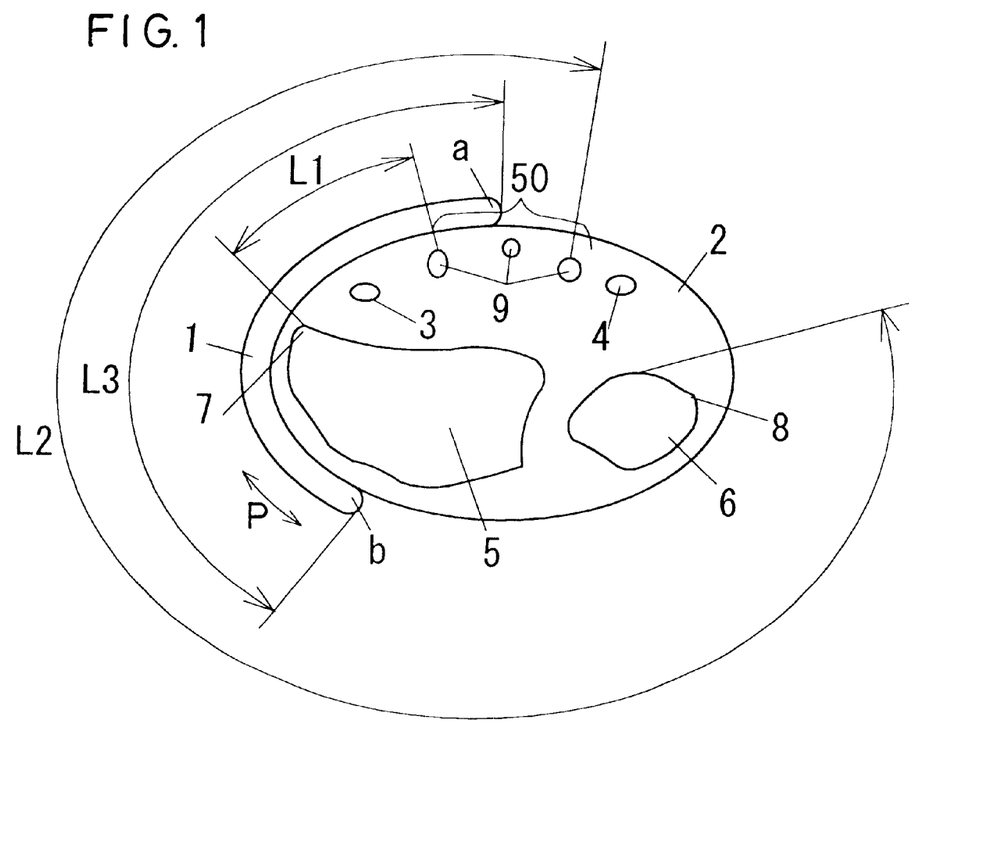
FIG. 1 is an explanatory view showing in a schematic section a mounting state of the air bag in an event of oppressing radial artery at a wrist of the user in an embodiment of the hemadynamometer according to the present invention.
Figure 2:
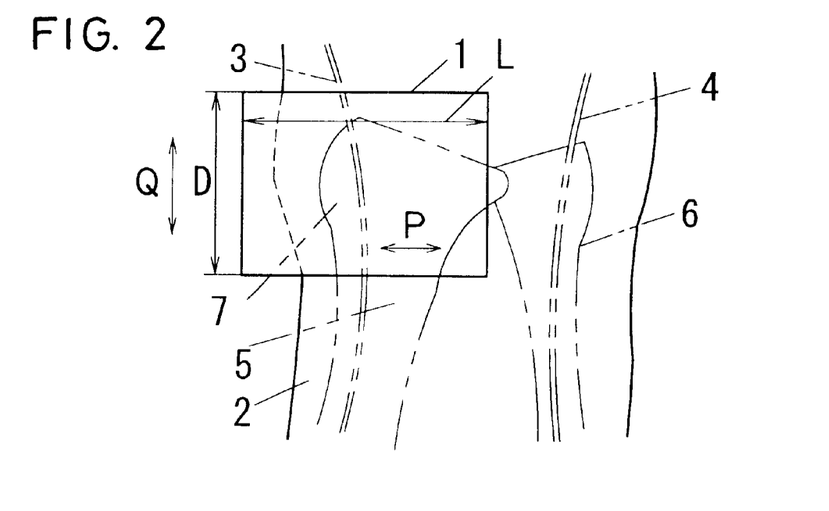
FIG. 2 is a schematic plan view on palm side of the wrist with the air bag of the hemadynamometer of FIG. 1 shown in the mounted state.

In the hemadynamometer in an embodiment of the present invention, an air bag 1 mountable on the user's wrist 2 along the peripheral direction P as shown in FIG. 1 comprises a rectangular bag member formed with such flexible material as urethanes, silicones or the like. In the drawing, the air bag 1 is shown in a schematic sectioned view in a state of being mounted on the wrist 2. On the other hand, FIG. 2 shows the air bag 1 in a top plan view. In this case, the air bag 1 has a length L and a width D, the length L being enough, when wound specifically on the side of radius 5 of the wrist 2 from such hard organization area 50 as tendons 9 on the palm side of the wrist 2 as a starting point, for passing over radial artery 3 which is adjacent to the radius 5 and reaching at least a styloid process 7 of the radius 5 but failing to reach an ulnar artery 4 adjacent to an ulna 6 having a styloid process 8 of the ulna 6, and the width D being enough for locally oppressing the radial artery 3 at least at a portion substantially right above the radial styloid process 7 in lengthwise direction of the wrist 2, so that the ulnar artery 4 will not be oppressed but the radial artery 3 only will be oppressed or subjected to the ischemia.

Further, the length of the air bag 1 in the peripheral direction P of the wrist can be properly variably set in a range from the maximum length L2 to the minimum length L1 as shown in FIG. 1, in which the maximum length L2 expands from an end "a" of the air bag 1 disposed, as the starting point, on one tendon 9 in the hard organization area 50 on the palm side and closest to the ulnar artery 4 (righthand side in FIG. 1) to the other forward end "b" of the air bag 1 terminating just before the ulnar artery 4 on the side of the radius 5 when the bag is wound over the radius 5, and the minimum length L1 expands from the closest tendon 9 in the hard organization area 50 to the radial artery 3 (lefthand side in FIG. 1) as the starting point to a point where the forward end "b" of the air bag 1 terminates reaching the radial styloid process 7 when the bag is wound on the side of the radius 5. Here, as shown in FIG. 1, the air bag 1 is set to be of a length L3 expanding from an intermediate tendon 9 in the hard organization area 50 on the palm side, as the starting point, through the radial styloid process 7 to a point covering about one half of the periphery of the wrist.

Accordingly, the air bag 1 is disposed as mounted on the wrist with the one end "a" positioned on the hard organization area 50 as the starting point and to be on the side of the radius 5, so as to oppress the radial artery 3 and radial styloid process 7 but not to oppress the ulnar artery 4, whereby the air bag 1 can be wound to enclose the radial styloid process 7 where the radial artery 3 is positioned closest to the surface of the living body, and the radial artery 3 only can be subjected to the ischemia without subjecting the ulnar artery 4 to the ischemia. It is thereby made possible to render the pulse signal caught by the air bag 1 to be accurate, since only the radial artery 3 among the two arteries present in the wrist is made to be oppressed. That is, the problems caused in the known arrangements due to the oppression of both arteries are eliminated, any influence due to an interference between the pulse signals from the two arteries is eliminated so as to reduce its influence on the precision of the blood pressure discrimination, highly reliable measurement of the blood pressure and pulse can be executed, and an accurate discrimination of the blood pressure value can be attained.

Further, as the length of the air bag 1 is set to be one expanding from such hard organization area 50 as the tendons 9 on the palm side of the wrist as the starting point at least to the radial styloid process 7, it is enabled to be responsive sufficiently to individual difference in the position of the radial artery 3, and to prevent any positional deviation of the air bag 1 during the pressurization or possible escape of the artery from occurring. At the same time, as the portion of ischemia by means of the air bag 1 is limited to be local, the user can be subjected to less oppressive sensation, the ischemia can be attained without being affected by the positional individual difference of the radial artery 3 in a range of 135 to 220 cm, for example, of the peripheral length of the wrist, and the ischemia can be executed by means of the ideal air bag 1 providing less burden to the user.

Figure 3:
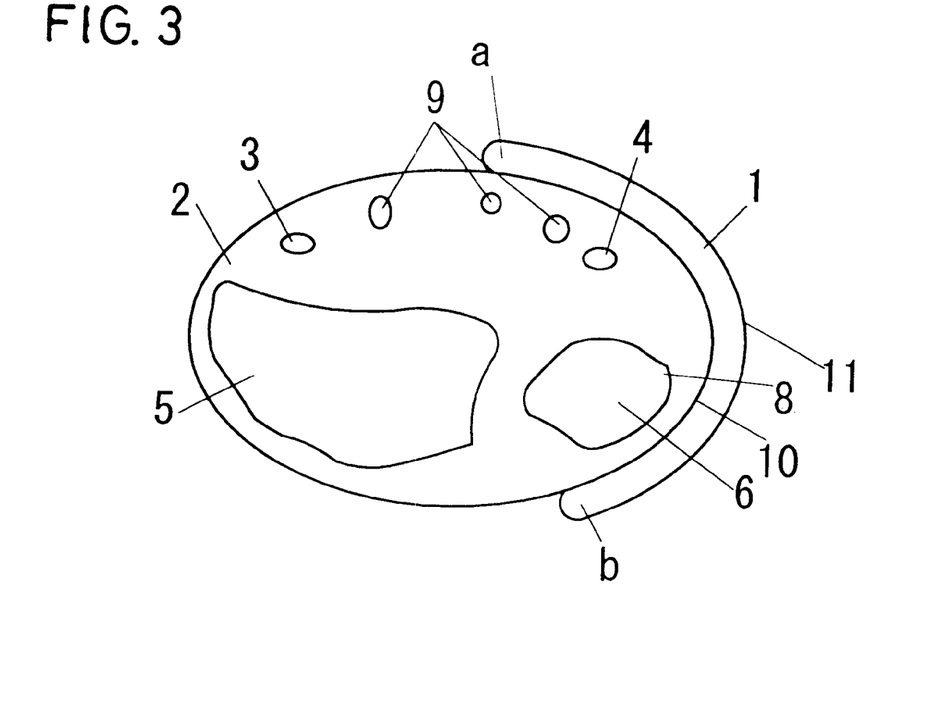
FIG. 3 is an explanatory view showing in a schematic section a mounting state of the air bag in an event of oppressing ulnar artery at the user's wrist in another embodiment of the present invention.
Figure 4:
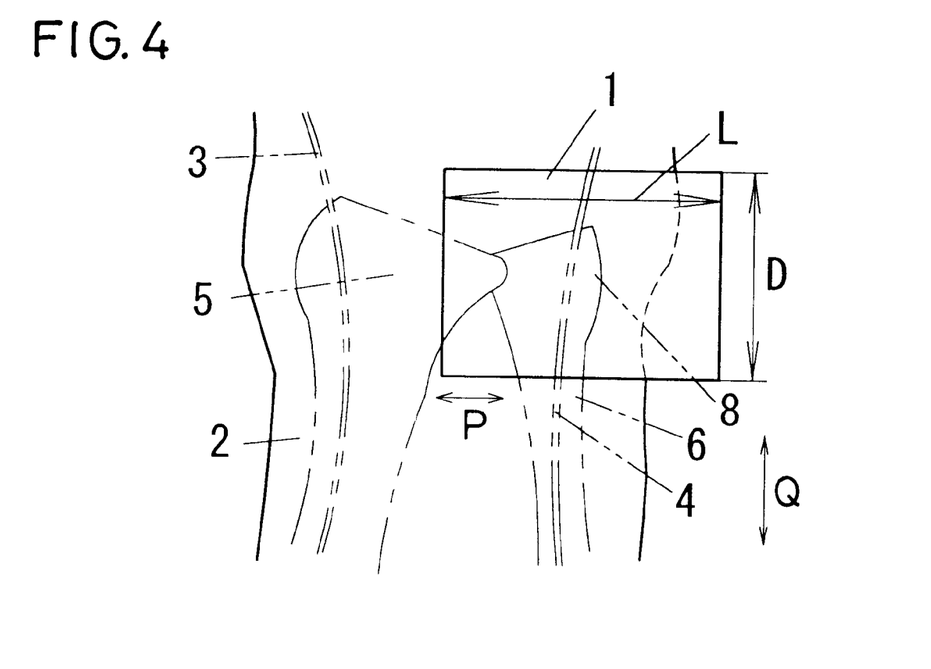
FIG. 4 is a schematic plan view on the palm side of the wrist with the air bag of the hemadynamometer of FIG. 3.

In FIGS. 3 and 4, there is shown another embodiment of the hemadynamometer according to the present invention, in which the air bag 1 has a length L and a width D, the length L expanding from such hard organization area 50 as the tendons 9 as the starting point of the bag wound on the side of the ulna 6 at least to the ulnar styloid process 8 reached by the bag's end but not reaching the radial artery 3, and the width D being capable of locally oppressing the ulnar artery 4 at least at a position substantially right above the ulnar styloid process 8 with respect to the lengthwise direction R of the wrist, so that the arrangement enables only the radial artery 3 to be oppressed or subjected to the ischemia, without causing the radial artery 3 to be oppressed, whereby it is enabled to attain the same function as in the foregoing embodiment of FIG. 1, by mounting the air bag 1 to the wrist so as to enclose the ulnar styloid process 8 where the ulnar artery 4 is positioned to be the closest to the living body surface, without subjecting the radial artery 3 to the ischemia but reliably attaining the ischemia of only the ulnar artery 4. Other respects of the arrangement in the embodiment of FIGS. 3 and 4 are the same as those in the embodiment of FIGS. 1 and 2, and the same reference figures as those in FIGS. 1 and 2 are given to the same constituting elements in FIGS. 3 and 4.

Next, when the air bag 1 is formed in a rectangular shape as in the foregoing embodiments and sheet members forming lower and upper surfaces 10 and 11 are of the same length, there arises a risk that wrinkles are caused to occur in the lower surface 10 when the air bag is pressurized, whereby the pressure is made not to be evenly transmitted to the surface of the wrist over the whole area of the air bag 1 and the blood pressure measurement cannot be performed accurately. According to the present invention, there is provided an embodiment which is effective to render the ischemia properties of the air bag more excellent.

Figure 5:
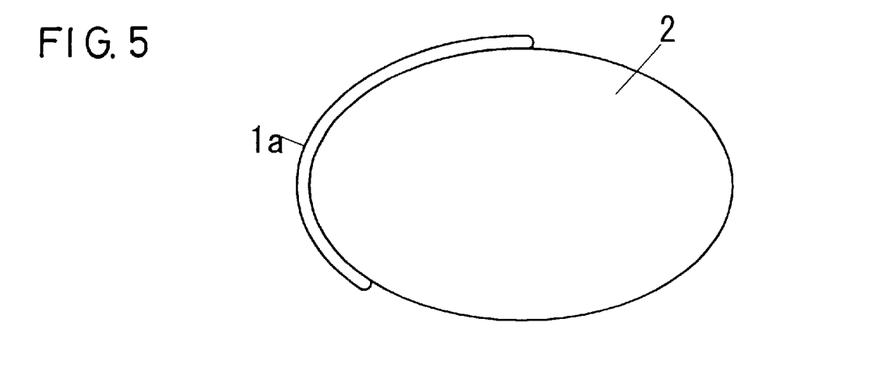
FIGS. 5 through 16 are respectively explanatory views of other embodiments according to the present invention.

In another embodiment shown in FIG. 5 of the present invention, the air bag 1a is formed as curved. In this case, the air bag 1a is to be prepared through a blow molding process or the like with a mold having a curved surface on the inner side. Since such curved air bag 1a includes less wrinkles in the lower surface upon pressurizing as compared with the air bag made with planar sheets mutually adhered, the air bag is excellent in the adhesion properties and pressure transmission efficiency with respect to the wrist, and the detecting precision of the pulse signal can be elevated.

Figure 6:
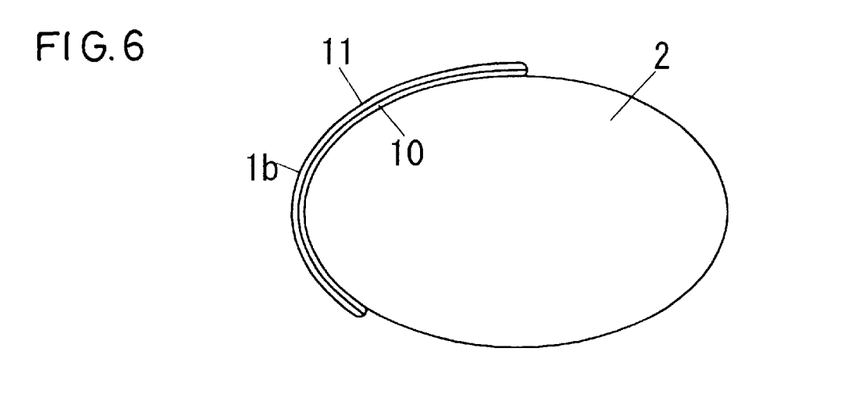

In another embodiment shown in FIG. 6, the air bag 1b is formed by adhering mutually edgewise an inside sheet forming the lower surface 10 (hereinafter "inside sheet 10") and an outside sheet forming the upper surface 11 (hereinafter "outside sheet 11") in curved shape so as to correspond to the shape of the wrist 2, whereby the air bag 1b is rendered easily manufacturable and excellent in the adhesion property and pressure transmitting efficiency with respect to the wrist 2.

Figure 7:
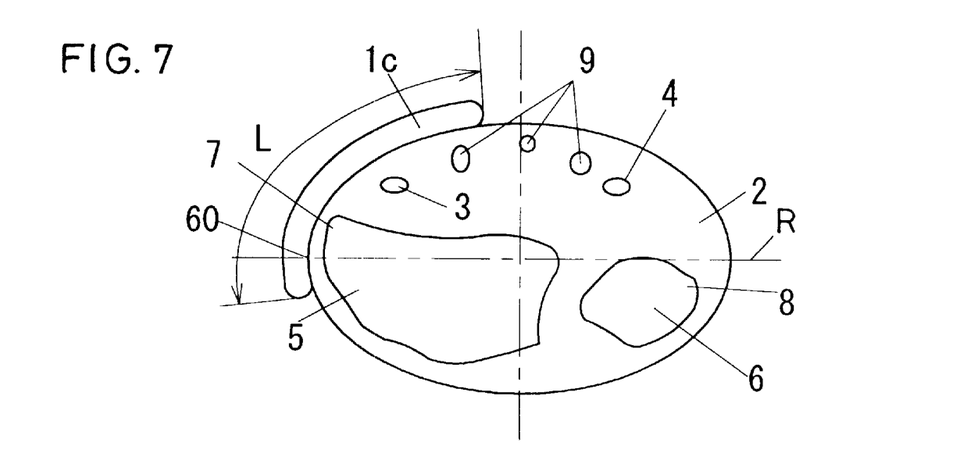

In another embodiment shown in FIG. 7, the air bag 1c is formed as arranged to be in a curved shape having a length L covering at least a quarter of the whole outer periphery of the wrist 2, expanding from one tendon 9 to the radial styloid process 7 through a cross point 60 of the major axis R of a cross section of the wrist 2 and the outer periphery of the wrist on the side of the artery to be subjected to the ischemia, whereby the air bag 1c is made excellent in the adhesion properties with respect to the radial styloid process 7 of a smaller curvature of radius in the wrist 2 and can be prevented from being positional deviated without giving to the user any oppressive sensation, so as to be excellent in the pressure transmitting efficiency. The same function can be attained even when the air bag 1c is arranged to be wound to expand from the tendon 9 to the ulnar styloid process 8.

Figure 8:
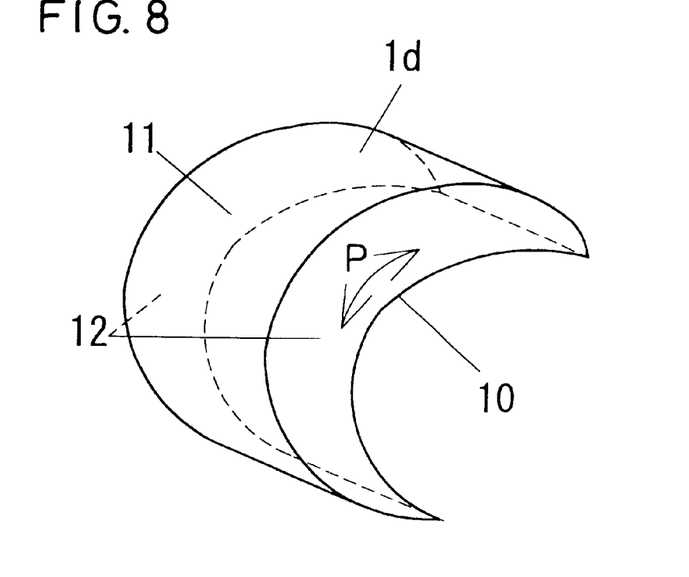
Figure 9:
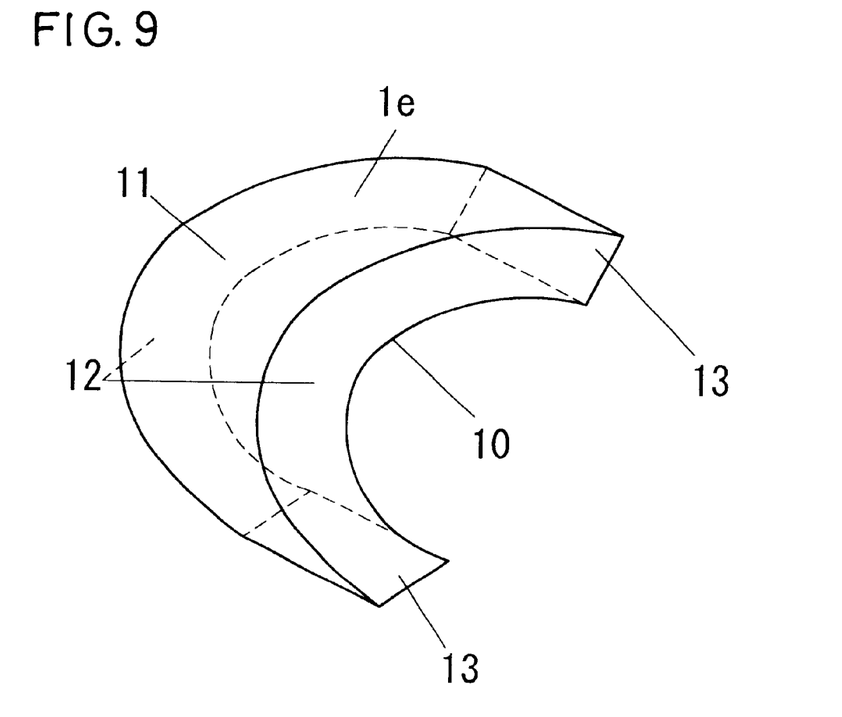

In another embodiment shown in FIG. 8, the air bag id is formed in a three-dimensional configuration by providing sheet-shaped side walls (hereinafter "side wall sheets 12") along peripheral direction P between the inside sheet 10 and the outside sheet 11. Accordingly, while in the case of the air bag formed by adhering mutually the planar sheets there arises a risk that the sheets are remarkably expanded upon being pressurized and a tension caused by a deformation due to such expansion gives to the interior pressure of the air bag an influence so as to reduce the oppressive force to the wrist, the air bag 1d according to the present embodiment is formed in the three-dimensional shape with the side wall sheets 12 lying in the peripheral direction P of the wrist between the inside and outside sheets 10 and 11, so that the reduction in the oppressive force due to the expansive deformation of the inside sheet 10 upon the pressurization can be compensated for by the displacement of the side wall sheets 12, and the ischemia can be executed in excellent manner. It is also possible to attain the same function even by providing the side wall sheets 12 to lie along the lengthwise direction Q of the wrist. Further, as shown in FIG. 9, it is also possible to provide the side wall sheets 12 and 13 respectively in both of the peripheral direction P and the lengthwise direction Q of the wrist, whereby it is enabled to secure the oppressive force to the artery due to still larger displacement upon the pressurization.

Figure 10:
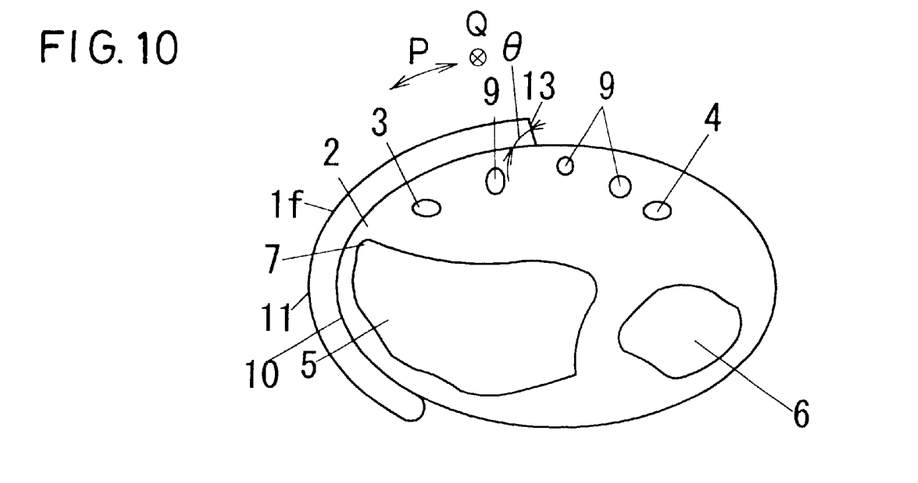

In another embodiment shown in FIG. 10, the air bag if is formed to define an acute angle θ by one of the side wall sheets 13 in the lengthwise direction of the wrist which is on the side of such hard organization area 50 as the tendons 9 on the palm side and the inside sheet 10. When the particular side wall sheet 13 defines an obtuse angle with respect to the inside sheet 10, the side wall sheet 13 is caused to swell upon being pressurized, so as to be able to contact the wrist 2 at a position right above the ulnar artery 4, to catch the pulse at this artery 4 and to cause an error to arise in the blood pressure measurement. In the present embodiment, the side wall sheet 13 in the swelled state is prevented from contacting the wrist 2 at its position right above the ulnar artery 4 so as not to be influenced directly by the pulse of the ulnar artery 4, and the blood pressure measurement can be prevented from involving any error.

While in the respective embodiments of the foregoing drawings the arrangement of the air bag wound on the side of the radius 5 has been shown as an example, it will be appreciated that any error in the blood pressure measurement caused by the pulsation of the radial artery 3 in an event when the air bag is wound on the side of the ulna 6 can be similarly prevented.

Figure 11:
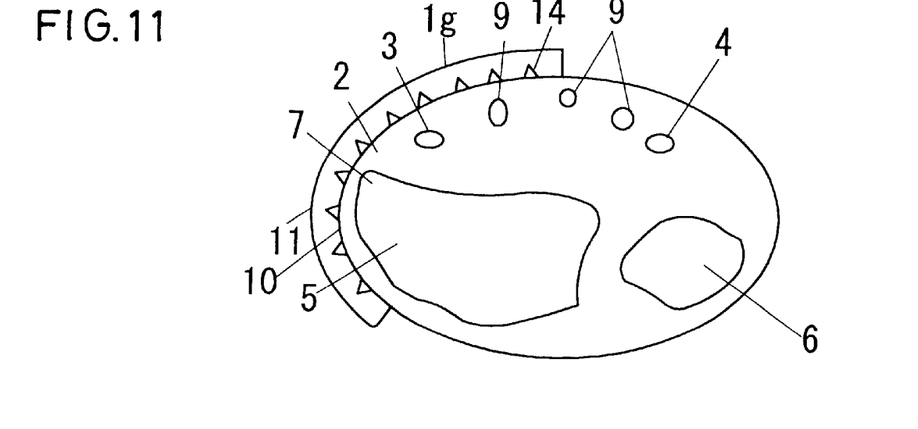
Figure 12:
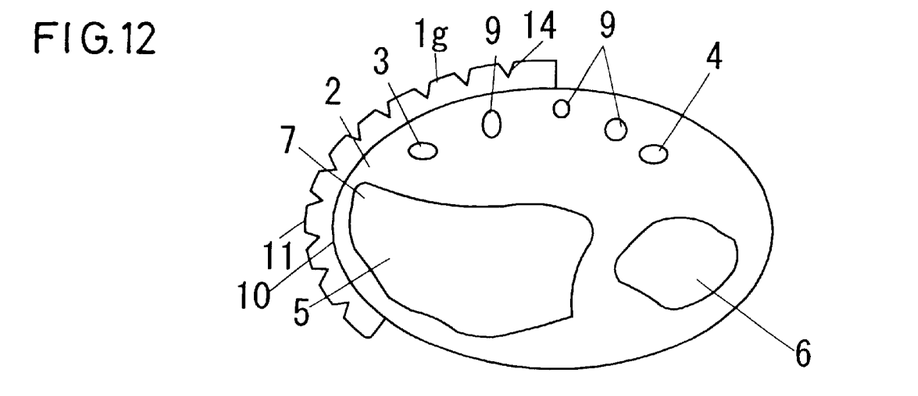
Figure 13:
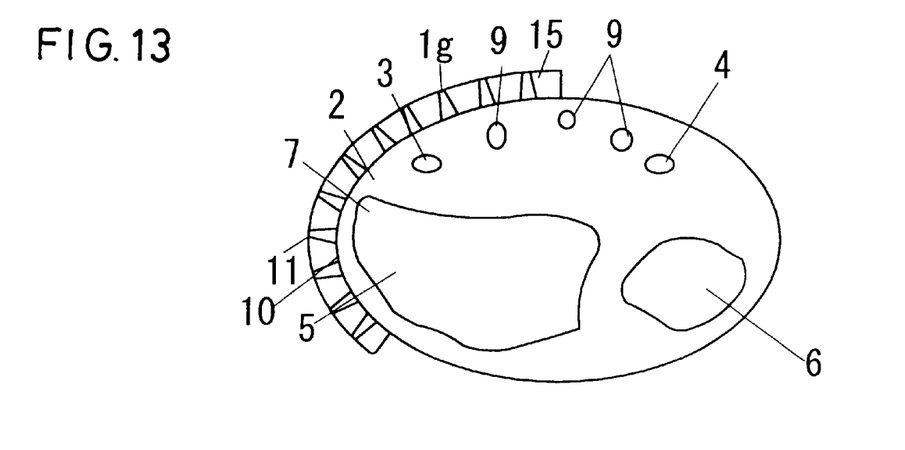

In another embodiment shown in FIG. 11, partitions 14 are provided to the inside sheet 10 of the air bag 1g, to form a plurality of air chambers divided in the peripheral direction P of the wrist 2. In general, the wrist is not elliptic precisely in its peripheral surface but is irregular, and an air bag having only a single air chamber is apt to cause a gap to occur between the bag and the wrist surface. When the inside sheet 10 of the air bag 1g is provided with such air chambers as shown in FIG. 11 to form the many air chambers, therefore, the adhesion properties of the air bag with respect to the wrist surface can be well improved. Further, the many air chambers may be formed by providing the partitions 14 to the outside sheet 11 as shown in FIG. 12 or it is also possible to form the air bag with a plurality of small or narrow air bags 15 mutually joined in the peripheral direction P of the wrist 2 as made to communicate with each other.

Figure 14:
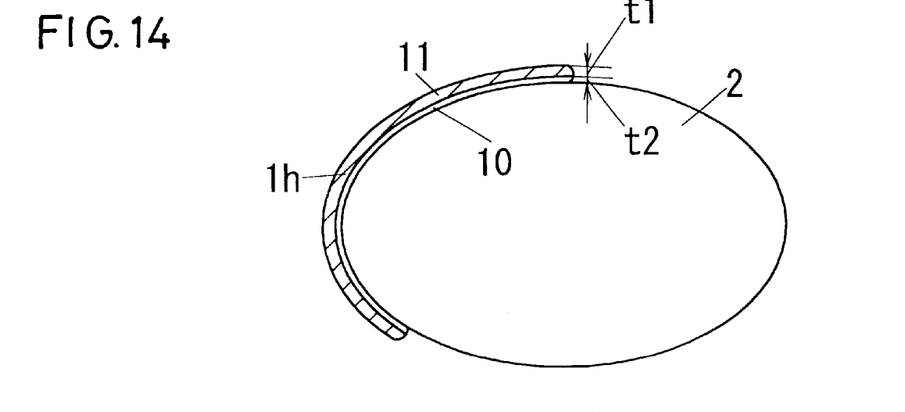

In another embodiment shown in FIG. 14, the inside and outside sheets 10 and 11 of the air bag 1h are formed with the same material, while the inside sheet 10 is made to be of a thickness t2 smaller than a thickness t1 of the outside sheet 11, whereby the inside sheet 10 is made more easily expansible than the outside sheet 11 upon being pressurized, so that the adhesion properties will be excellent and the pressure transmission efficiency can be elevated.

Figure 15:
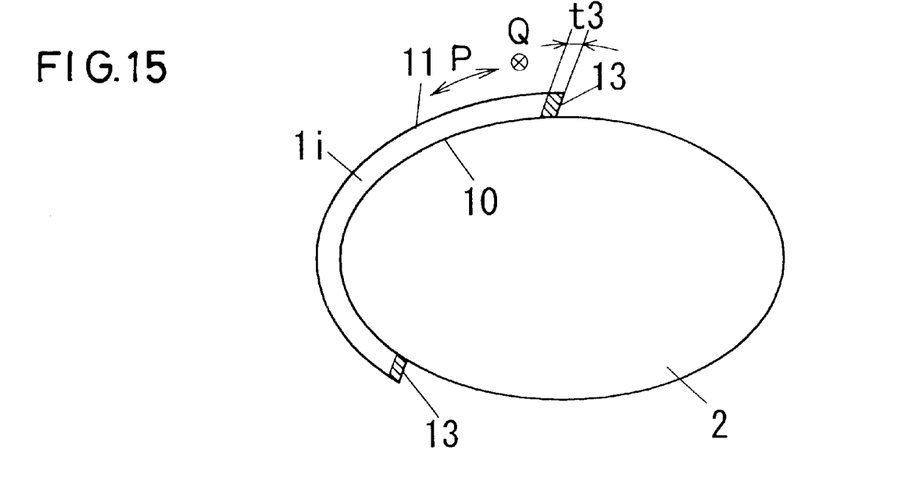

In another embodiment shown in FIG. 15, the air bag 1i is formed to have a larger thickness t3 at the side wall sheets 13 lying in the lengthwise direction Q than the inside and outside sheets 10 and 11, whereby the swell of the inside sheet 10 is made larger than the side wall sheets 13 in the lengthwise direction of the wrist, and the pressure transmission towards the arteries in the wrist is more efficient. Further, it is possible to attain the same function even when the side wall sheets 12 lying in the peripheral direction P are made thicker than the inside and outside sheets 10 and 11 or when both side wall sheets 12 and 13 in both of the peripheral and lengthwise directions P and Q are made thicker than the inside and outside sheets 10 and 11.

Figure 16:
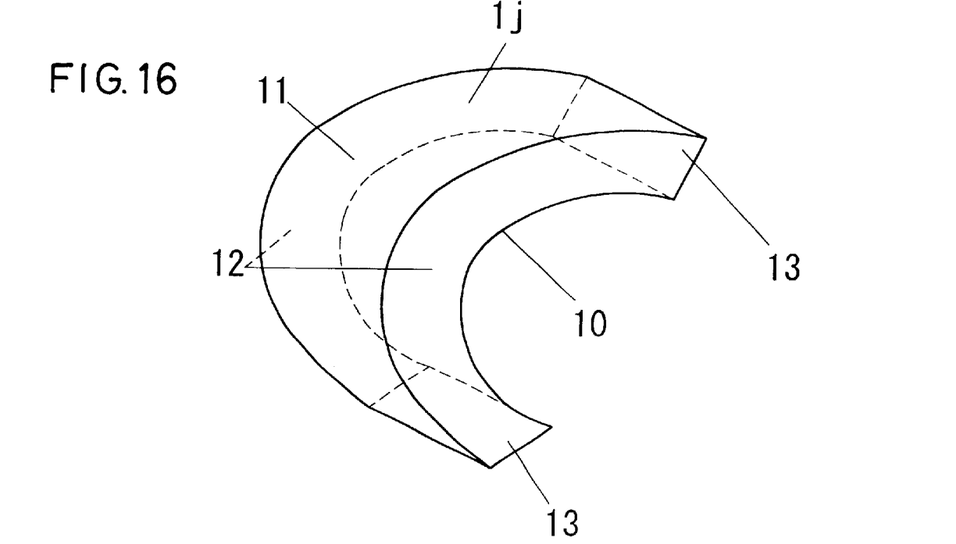

In another embodiment shown in FIG. 16, the inside sheet 10 of the air bag 1j is formed with a material higher in the stretchability than the outside sheet 11, so that the oppression force of the inside sheet 10 to the artery in the wrist 2 upon pressurization can be enlarged.

Figure 17:
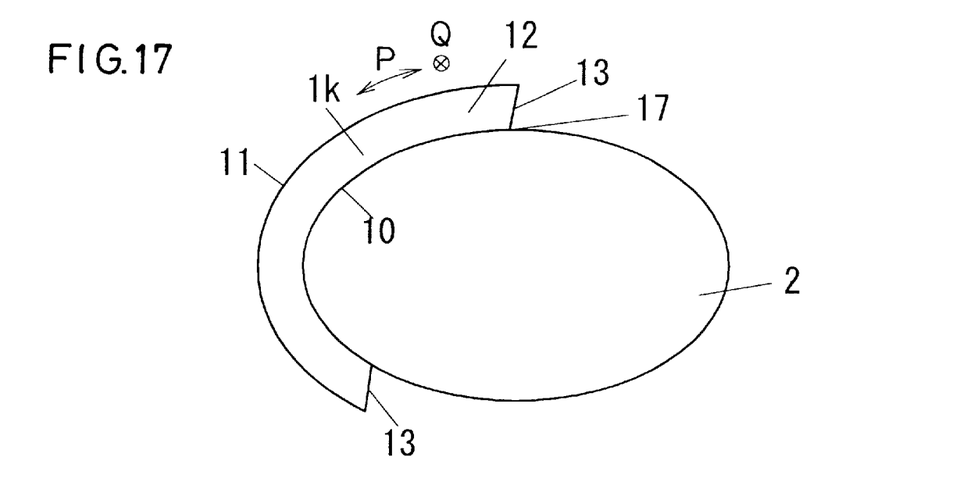
FIG. 17 is an explanatory sectional view in mounted-state of the air bag in another embodiment of the present invention.
Figure 18:
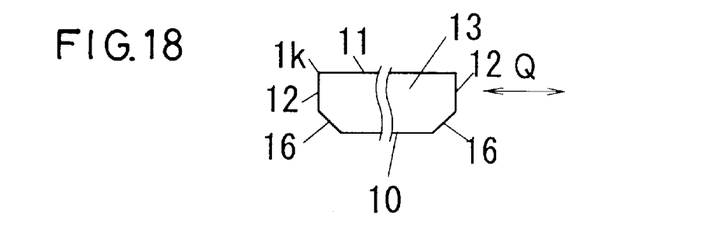
FIG. 18 is a schematic view of the hemadynamometer in FIG. 17 as viewed in the lengthwise direction of the wrist with part shown as omitted.

In another embodiment shown in FIGS. 17 and 18, the air bag 1k is formed to be provided with a curvature at joint parts 16 of the side wall sheets 12 in the peripheral direction P of the wrist with the inside sheet 10, whereby the oppression force of the inside sheet 10 to the artery in the wrist 2 can be further enlarged. At the same time, any concentration of stress occurring at the joint parts 16 upon the pressurization is made less and the air bag 1k is improved in the durability. Further, the curvature may be provided at joint parts 17 of the side wall sheets 13 disposed along the wrist's lengthwise direction Q with the inside sheets 10, or even at both of the joint parts 16 and 17.

Figure 19:
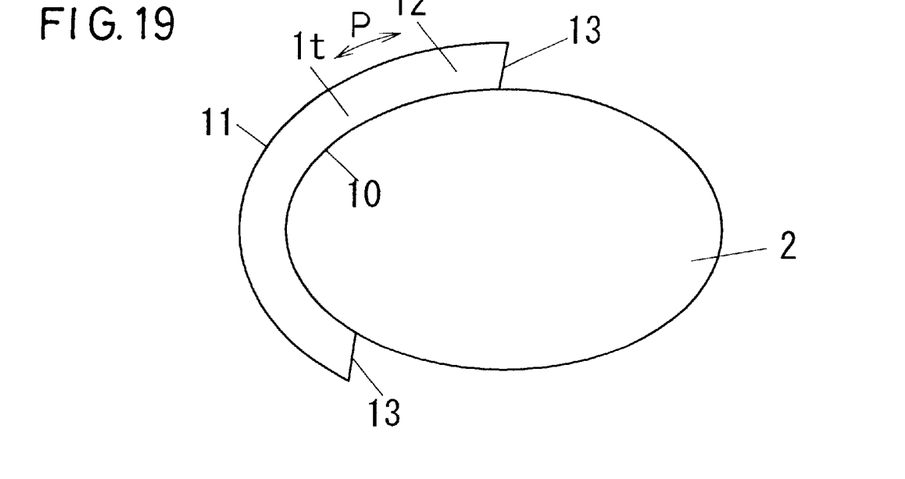
FIG. 19 is a schematic explanatory view for another embodiment of the present invention.
Figure 20:
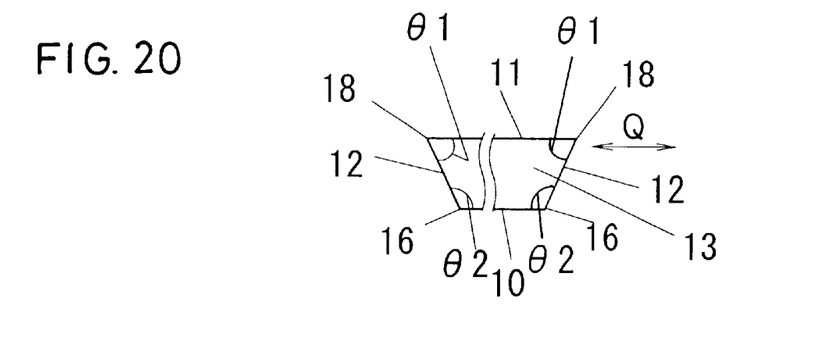
FIG. 20 is a schematic view of the hemadynamometer in FIG. 19 as viewed in the lengthwise direction of the wrist with part shown as omitted.

In another embodiment shown in FIGS. 19 and 20, the air bag 1t is formed in a three dimensional shape, in which joint parts 18 of the side wall sheets 12 in the wrist's peripheral direction P with the outside sheet 11 define an acute angle θ1 while the joint parts 16 of the side wall sheets 12 in the wrist's peripheral direction P with the inside sheet 10 define an obtuse angle θ2, whereby any stress concentration occurring at the joint parts 16 upon pressurization is made less and the air bag it can be made excellent in the durability.

Figure 21:
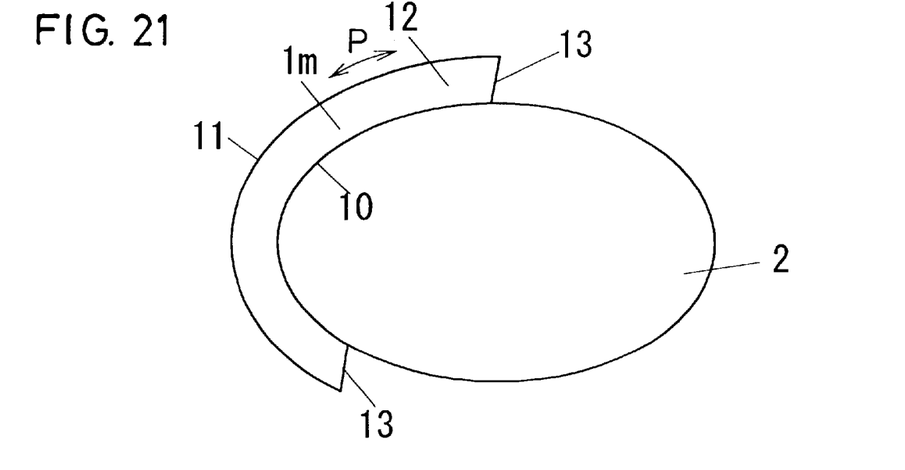
FIG. 21 is a schematic explanatory view for still another embodiment of the present invention.
Figure 22:
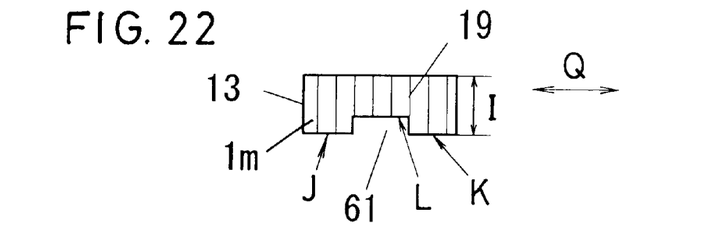
FIG. 22 is a schematic view of the hemadynamometer in FIG. 21 as viewed in the lengthwise direction of the wrist.

In another embodiment shown in FIGS. 21 and 22, the inside and outside sheets 10 and 11 of the air bag 1m are coupled to each other with thin fibers 19 consisting of an elastic material or the like, and the distance I between the inside and outside sheets 10 and 11 is so varied in the wrist's lengthwise direction Q by the fibers 19 that the distance I at intermediate zone L between a zone closest to the wrist joint (hereinafter "closer zone J") and a zone farthest from the wrist joint (hereinafter "farther zone K") will be smaller than the closer and farther zones J and K, so as to form a dent 61 in the inside surface. When the air bag is pressurized to inflate it with air or the like gas, in general, the swell is the largest at central zone and is smaller in both end zones, so that a positional deviation of the air bag gives a remarkable affection on the ischemia of the artery. With the air bag 1m of the present embodiment, however, the swell at the central intermediate zone L including the dent 61 and the swell at the closer zone J and at the farther zone K will be equivalent, so that the affection of positional deviation of the air bag 1m in the wrist's lengthwise direction Q will be less and the error in the blood pressure measurement can also be reduced.

Figure 23:
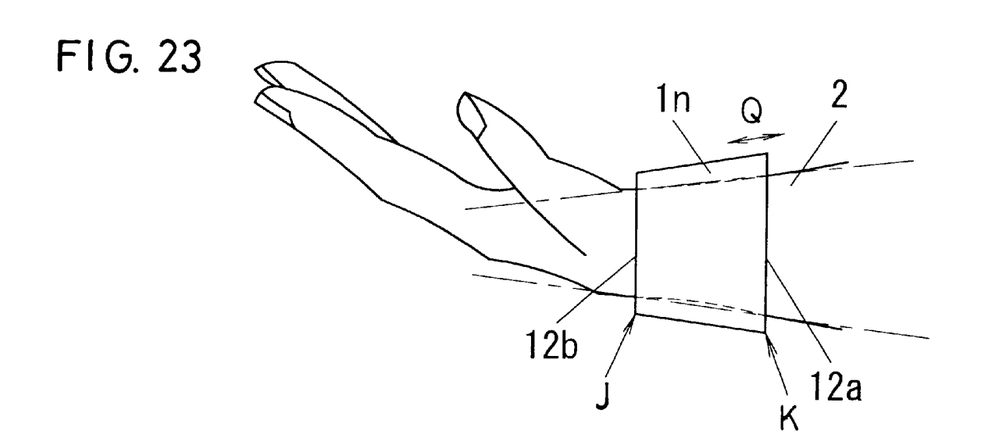
FIG. 23 is an explanatory view of still another embodiment of the present invention in a state of being used.
Figure 24:
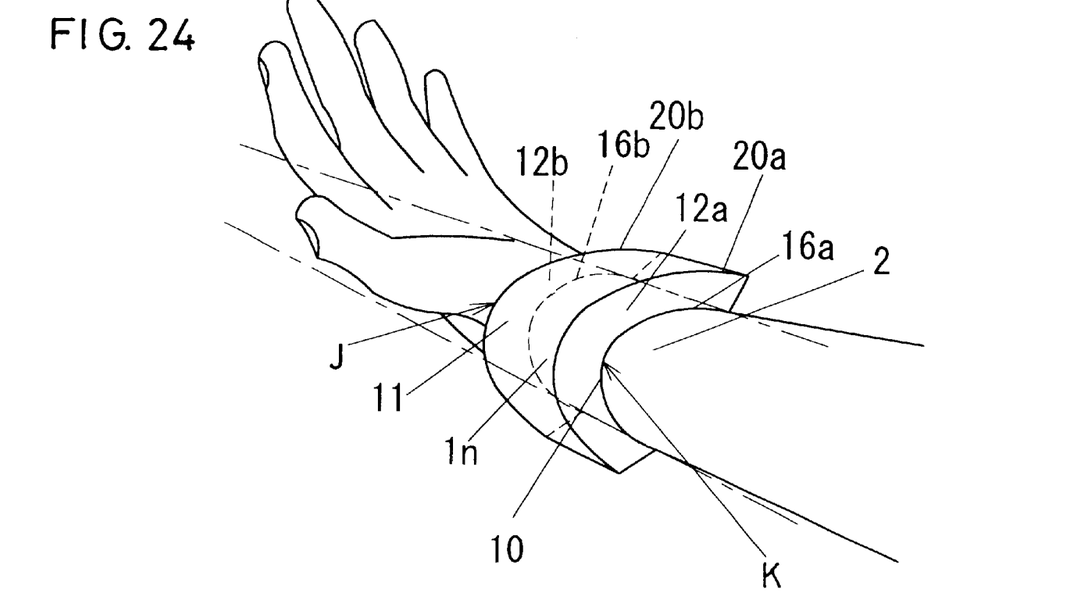
FIG. 24 is a perspective view of the hemadynamometer of FIG. 23 in the state of use.

In another embodiment shown in FIGS. 23 and 24, the air bag In is adapted to the fact that, in general, the peripheral length of the wrist at the closer zone J is shorter than that at the farther zone K. Thus, in the air bag in, the peripheral length at the joint part 16b in the closer zone J of the inside sheet 10 with the side wall sheet 12b is made shorter than the peripheral length at the joint part 16a in the farther zone K of the inside sheet 10 with the side wall sheet 12a. At the same time, the peripheral length at a joint part 20b in the closer zone J of the outside sheet 11 with the side wall sheet 12b is made shorter than the peripheral length at a joint part 20a in the farther zone K of the outside sheet 11 with the side wall sheet 12a. Consequently, the air bag 1n can be further improved in the adhesion property to the wrist 2.

Figure 25:
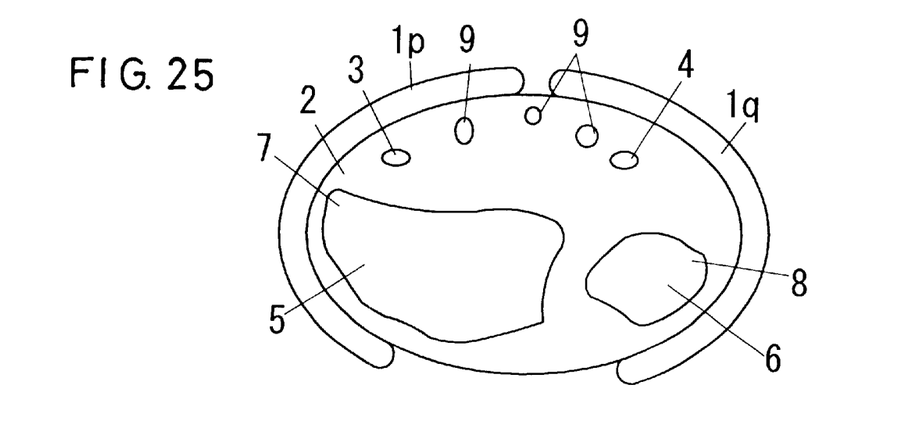
FIG. 25 is a schematic explanatory view for still another embodiment of the present invention.

In another embodiment shown in FIG. 25, the hemadynamometer of the present invention comprises an air bag 1p for oppressing one artery to be used in measuring the pulse and blood pressure, and an auxiliary air bag 1q for oppressing the other artery to be not used in measuring the pulse and blood pressure. The air bag 1p is wound on the side of radius 5 for measuring the pulse and blood pressure at the radial artery 3, while the auxiliary air bag 1q is wound on the side of ulna 6 to keep the ulnar artery 4 in the ischemia state during the measurement at the radial artery 3, and a quick air exhaust of both air bags 1p and 1q is performed as the measurement terminates. With this arrangement, the blood pressure and pulse values thus measured at the radial artery 3 are not influenced by the ulnar artery 4. The arrangement may be reversed to wind the air bag 1p on the side of the ulna 6 for the measurement of pulse and blood pressure at the ulnar artery 4, while the auxiliary air bag 1q keeps the radial artery 3 in the ischemia state during the measurement.

Figure 26:
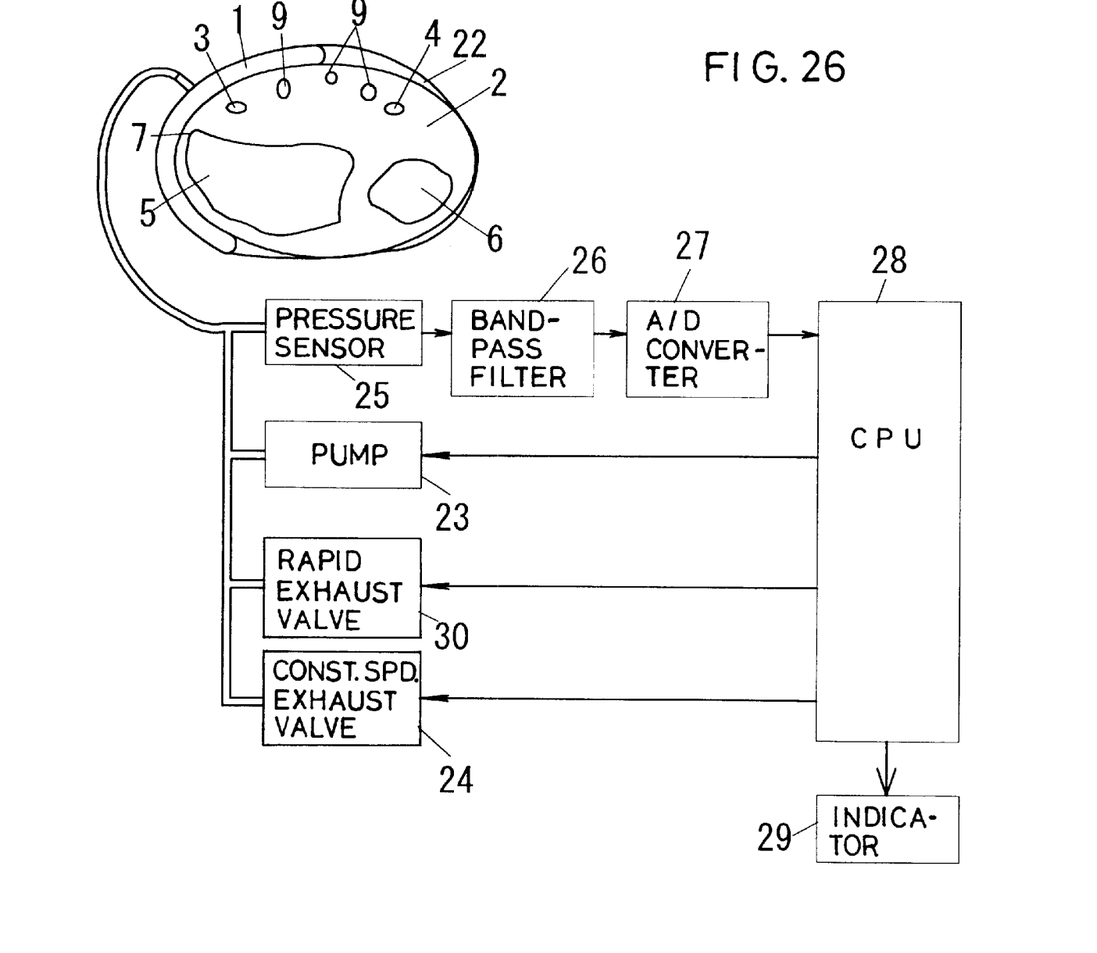
FIG. 26 is a schematic block diagram showing a structure of the hemadynamometer in FIG. 25.

In another embodiment shown in FIG. 26, there is shown a wrist-type hemadynamometer system, which comprises the air bag 1 wound on the user's wrist 2 from the area of tendons 9 over the radial styloid process 7 to the radius 5, a band 22 for securing the air bag 1 on the wrist 2, a pneumatic pump 23 for pressurizing the air bag 1 until the ischemia of the radial artery 3 is reached, a constant speed exhaust valve 24 for gradually exhausting the bag after the ischemia reached, a pressure sensor 25 for detecting pulse signals at the radial artery 3 as superposed on the interior pressure of the air bag 1, a band pass filter 26 of, for example, 0.5–10 Hz with respect to the detected pulse signal, an A/D converter 27 for digitalizing the pulse signal through a sampling of, for example, 50 Hz, a CPU 28 for discriminating the blood pressure, a display 29 for displaying measured values after termination of the blood pressure measurement, and a quick exhaust valve 30 for quickly exhausting the air bag 1. After winding the air bag 1 from right above the tendon area over the radius 5 and securing the bag on the wrist 2 with the band 22, the pump 23 pressurizes the bag up to, for example, 480 mmHg until the ischemia state of the radial artery 3 is reached, then the constant speed exhaust pump 24 reduces the pressure at a rate of, for example, 3 mmHg/sec, during which only the pulse at the radial artery 3 as superposed on the interior pressure of the air bag 1 is extracted at the pressure sensor 25 and band pass filter 26. The pulse signal is taken up through the A/D converter 27 into the CPU 28 as digital signals, and the pulse number and the highest and lowest blood pressures are discriminated there and are displayed at the display 29. In the present embodiment, further, it is possible to perform the same blood pressure measurement even with the air bag 1 wound on the side of the ulna 6 and with the pulse attained at the ulnar artery 4.

What is claimed is:

1. A hemadynamometer for attaining arterial oppression for ischemia with an air bag adapted to be wound on a part of a wrist of a user in its peripheral direction, in which the air bag is adapted to oppress only one of two arteries including ulnar and radial arteries in the wrist with a length of the air bag in the wrist's peripheral direction being enough, when the air bag is wound on the user's wrist from a hard area including tendons on palm side as a start point towards the one of the two arteries which is subject to ischemia, for passing over the one artery and reaching at least the styloid process of one of two bones at the wrist in a minimum length L1 but not reaching the other artery not subject to the ischemia in a maximum length L2, and with a width in the wrist's lengthwise direction being enough for locally oppressing the one artery subject to the ischemia at a position substantially right above the styloid process of the bone on the one artery side, wherein the air bag includes curved upper and lower surface parts with the lower surface part of the air bag made dearer than the upper surface part.

2. A hemadynamometer for attaining arterial oppression for ischemia with an air bag adapted to be wound on part of a wrist of the user in its peripheral direction, in which the air bag is adapted to oppress only one of two arteries including ulnar and radial arteries in the wrist with a length of the air bag in the wrist's peripheral direction being enough, when to air bag is wound on die user's wrist from a hard area including tendons on palm side as a start point towards the one of the two arteries which is subject to ischemia, for passing over the one artery and reaching at least tile styloid process of one of two bones at We wrist in a minimum length L1 but not reaching the other artery non-subject to the ischemia in a maximum length L2, and wit a width in the wrist's lengthwise direction being enough for locally oppressing the one artery subject to the ischemia at a position substantially right above the styloid process of the bone on the side of the artery subject to the ischemia, wherein tile air bag includes curved upper and lower surface parts with the air bag made in a three-dimensional shape including upper and lower surface pans formed as curved in the peripheral direction of the user's wrist, and at least a side wall part provided between and continuing to the upper and lower surface parts and lying in one of peripheral and lengthwise directions of the wrist with the side wall parts of the air bag made. thicker than the upper and lower surface pans.

3. A hemadynamometer for attaining arterial oppression for ischemia with an air bag dad to be wound on part of a wrist of the user in its peripheral direction, in which the air bag is adapted to oppress only one of two arteries including ulnar and radial arteries in the wrist with a length of the air bag in the wrist's peripheral direction being enough, when the air bag is wound on the user's wrist from a hard area including tendons on palm side as a start point towards the one of the two arteries which is subject to ischemia, for passing over the one artery and reaching at least the styloid process of one of two bones at the wrist in a minimum length L1 but not reaching the other artery non-subject to the ischemia in a minimum length L2, and with a width in the wrist's lengthwise direction being enough for locally oppressing the one artery subject to ischemia at a position substantially right above the styloid process of the bone on the side of the artery subject to the ischemia, wherein the air bag includes curved upper and lower surface parts with the lower surface pad of the air bag formed with a material having a higher stretchability than the upper surface part.

* * * * *